(12) United States Patent
Weitkamp et al.

(10) Patent No.: US 12,708,393 B2
(45) Date of Patent: Aug. 18, 2026

(54) SURGICAL INSTRUMENT FOR MINIMALLY INVASIVE SURGERY

(71) Applicant: Sutter Medizintechnik GmbH, Emmendingen (DE)

(72) Inventors: Dirk Weitkamp, Waldkirch (DE); Thomas Dunz, Teningen (DE); Lothar Mitzlaff, Lagos (PT); Michael Thoss, Nagold (DE); André Fichtner, Wildberg (DE)

(73) Assignee: Sutter Medizintechnik GmbH, Emmendingen (DE)

( * ) Notice: Subject to any disclaimer, the term of this patent is extended or adjusted under 35 U.S.C. 154(b) by 989 days.

(21) Appl. No.: 17/959,626

(22) Filed: Oct. 4, 2022

(65) Prior Publication Data

US 2023/0310016 A1 Oct. 5, 2023

(30) Foreign Application Priority Data

Apr. 1, 2022 (DE) ..................... 10 2022 107 839.6

(51) Int. Cl.

| | |
|---|---|
| ***A61B 17/28*** | (2006.01) |
| ***A61B 17/29*** | (2006.01) |
| ***A61B 18/14*** | (2006.01) |
| *A61B 17/00* | (2006.01) |

(52) U.S. Cl.

CPC *A61B 17/2841* (2013.01); *A61B 2017/00367* (2013.01); *A61B 2217/007* (2013.01)

(58) Field of Classification Search

CPC .... A61B 2017/2939; A61B 2017/2936; A61B 2017/2926; A61B 2017/2945; A61B 2017/2932; A61B 2017/2938; A61B 2017/2918; A61B 18/085; A61B 18/1445; A63B 60/14

See application file for complete search history.

(56) References Cited

U.S. PATENT DOCUMENTS 5,575,805 A * 11/1996 Li .......................... A61B 17/29 606/174
2006/0052777 A1* 3/2006 Dumbauld ............. A61B 17/29 606/171

* cited by examiner

*Primary Examiner* — Majid Jamialahmadi
(74) *Attorney, Agent, or Firm* — Budzyn IP Law, LLC

(57) ABSTRACT

A surgical instrument comprising two jaw portions, at least one of which is rotatably mounted via an axis of rotation at a distal end of a shaft and is connected via a traction cable or a push rod to a gripping portion at the proximal end of the shaft, wherein the jaw formed by the jaw portions is held in an open or closed position by means of a suspension when the instrument is at rest.

7 Claims, 11 Drawing Sheets

SURGICAL INSTRUMENT FOR MINIMALLY INVASIVE SURGERY

The invention relates to a surgical instrument for minimally invasive surgery.

BACKGROUND

Surgical tweezers, forceps or coagulation instruments are used in minimally invasive surgery, for example, to grip or coagulate tissue. Such an instrument is known for example from DE 100 31 773 A1.

Described therein is a surgical instrument comprising two gripping portions, which are foldable together and foldable apart for gripping like forceps in and against a gripping direction. At least one gripping portion has at one end a first and second leg, each with a bending region, which are spaced from one another in the gripping direction, wherein at least the first leg of each gripping portion is arranged within a guide sleeve and is movable in the longitudinal direction of the guide sleeve relative to the second leg of the gripping portion such that when the legs move relative to one another in their longitudinal direction, the respective gripping portion is movable in the gripping direction.

There is a need for such a surgical instrument, which is preferably provided for one-time use, i.e. not for reuse. For this, it is advantageous to forego metallic rotary or milling portions without affecting the functionality of the instrument.

An object of the present invention is to provide an easy-to-manufacture surgical instrument of the aforementioned type with comprehensive functionality.

SUMMARY OF THE INVENTION

In a first aspect, the present invention relates to a surgical instrument comprising two jaw portions, at least one of which is rotatably mounted via an axis of rotation at a distal end of a shaft and is connected via a traction cable or a push rod to a gripping portion at the proximal end of the shaft, wherein the jaw formed by the jaw portions is held in an open or closed position by means of a suspension when the instrument is at rest. During a longitudinal movement (push or pull) of the traction cables or push rods, at least one jaw portion is rotated around the axis of rotation and the distal ends are moved away from one another (opening) or towards one another (closing). The instrument is preferably formed in such a way that the jaw formed by the jaw portions is held in an open position by a spring force when the instrument is at rest. In an alternative embodiment, the instrument is formed in such a way that the jaw formed by the jaw portions is held in a closed position by a spring force when the instrument is at rest. This improves the operability of the instrument. Overall, the present invention makes it possible to provide, for example, single-use instruments with properties that are not inferior to those of reusable instruments with a more complex design.

In one embodiment, the suspension comprises spring elements that each connect one of the jaw portions to the traction cable or the push rod. In one embodiment, the spring elements contain leaf springs or leaf spring sections as an extension of the shaft. In a further embodiment, the suspension alternatively or additionally comprises at least one spring arm and/or a compression spring in the gripping portion. Due to each of these configurations of a single-joint construction supported by spring force, the jaw portions can each be mounted on the distal end of the shaft via only one axis of rotation. In one embodiment, the axis of rotation comprises a hole, a bore or a recess. This not only reduces the constructive effort, but also has the consequence that no second joint has to be provided, which goes beyond the radial dimensions of the shaft when the instrument is operated and when the gripping portion is actuated.

In one embodiment, the spring elements are each materially connected to the traction cable or the push rod. In a further embodiment, the spring elements and the respective jaw portions are integrally designed. In a further embodiment, the spring elements are integrally designed with the traction cable or the push rod. In an alternative embodiment, the jaw portions are each cohesively and/or integrally connected to the traction cable or the push rod. Because of each of these configurations, the traction cables or push rods and the jaw portions with the spring elements or the jaw portions and the traction cables or push rods are firmly connected to one another. As a result, the electrical conductivity and the thermal conductivity of the instrument can be improved. In particular, it is possible to galvanically coat the traction cables/push rods and jaw portions, preferably completely or partially, without reducing the electrical or thermal conductivity at connection points or joint portions. Improved thermal conductivity leads to better heat dissipation from the distal end of the jaw portions, which in turn reduces the risk of the jaw portions adhering to the tissue to be treated. Thus, the present invention enables improved surgery.

Against this background, it can be viewed as another or alternative object of the present invention to provide a surgical instrument of the aforementioned type which prevents or reduces an adhesion of tissue in a surgical procedure. In particular, the electrical properties and thermal conductivity of such a surgical instrument are to be improved.

In one embodiment, the instrument can also have an electrical connector and/or a rinsing connector for supplying a rinsing liquid, wherein the electrical connector and/or the rinsing connector are provided in the direction of the user, in particular at the proximal end of the gripping portion or alternatively in the form of a cable firmly connected to the proximal end of the gripping portion. Integrating an electrical connector and/or a rinsing connector directly into the instrument extends the functionality of the instrument. Furthermore, this embodiment allows the provision of a multifunctional instrument with a small space requirement.

As a second, independent aspect, the solution to the object mentioned at the outset consists in a surgical instrument comprising two jaw portions, each of which is connected to an actuating element via a traction cable or a push rod, wherein the actuating element is arranged in a gripping portion at the proximal end of the instrument and at least has a spring element which can be deformed by actuation of the gripping portion, wherein a deformation of the spring element leads to an actuation of the actuation element within the gripping portion and thereby exerts a pulling or pushing force on the traction cables or push rods. Accordingly, according to the second aspect of the invention, a spring is also provided, which is preferably configured and arranged in such a way that the jaw formed by the jaw portions is held in an open position when the instrument is at rest. Alternatively, the suspension can be designed in such a way that the jaw is held in a closed position when the instrument is at rest.

In one configuration, the actuating element is formed by a component displaceable within the gripping portion in the axial direction of the instrument, which is designated here as a displacement carriage. The spring element is preferably formed by at least one spring arm whose one end is connected to the displacement carriage, and whose other end is applied to an inside of the gripping portion or is movably connected to it. This end of the spring arm is spaced from the displacement carriage when at rest. When the gripping portion is actuated, i.e. compressed, this end of the spring arm is pressed radially inwards, wherein this radial movement of this end of the spring arm is translated into an axial movement of the displacement carriage, which can be seen from the drawings of the spring arm described below.

A further aspect of the present invention relates to the fixing and actuation of the traction cables or push rods in the gripping portion of the instrument. For this purpose, a one-part or multi-part displacement carriage is provided, with integrated or connected spring elements for opening and closing the gripping portion. The displacement carriage is designed and arranged in the gripping portion such that compressing the gripping portion exerts a pull force on the traction cables or push rods, whereby the jaw portions are moved into the closed or open position depending on the constructive configuration.

This further aspect can be combined with the second aspect described above.

In one embodiment, the traction cables or the push rods are each attached to the displacement carriage by a driver, in particular a clamping bush. The drivers can be configured as clamping bushes and are therefore easy to produce and allow for easy assembly. The drivers also enable the jaw portions to be adjusted without play by adjusting the fixing points in the displacement carriage.

In one embodiment, the at least one spring arm rests against the inner walls of the gripping portion or is movably connected thereto. A restoring force is generated by the spring arm, by which the gripping portion and thus the jaw portions are brought into a rest position or held in this position. The adjustable drivers in the integrated spring also contribute to compensating for tolerances during production and assembly and enable the jaw portions to be adjusted without play.

In one embodiment, additional spring portions, in particular one or a plurality of compression springs, are provided in order to increase the spring force of the at least one spring arm or an alternative spring arm or to represent the sole suspension. This increases the restoring force in the rest position.

In one configuration, two spring arms are provided, which are arranged on opposite sides of the gripping portion. With such a two-armed configuration, a higher restoring force is also exerted in the rest position. In addition, an actuation, i.e. a compression of the gripping portion, is better translated into a displacement of the displacement carriage.

The invention is explained in more detail below with reference to the plurality of exemplary embodiments.

BRIEF DESCRIPTION OF THE DRAWINGS

In which.

DETAILED DESCRIPTION

Figure 1:
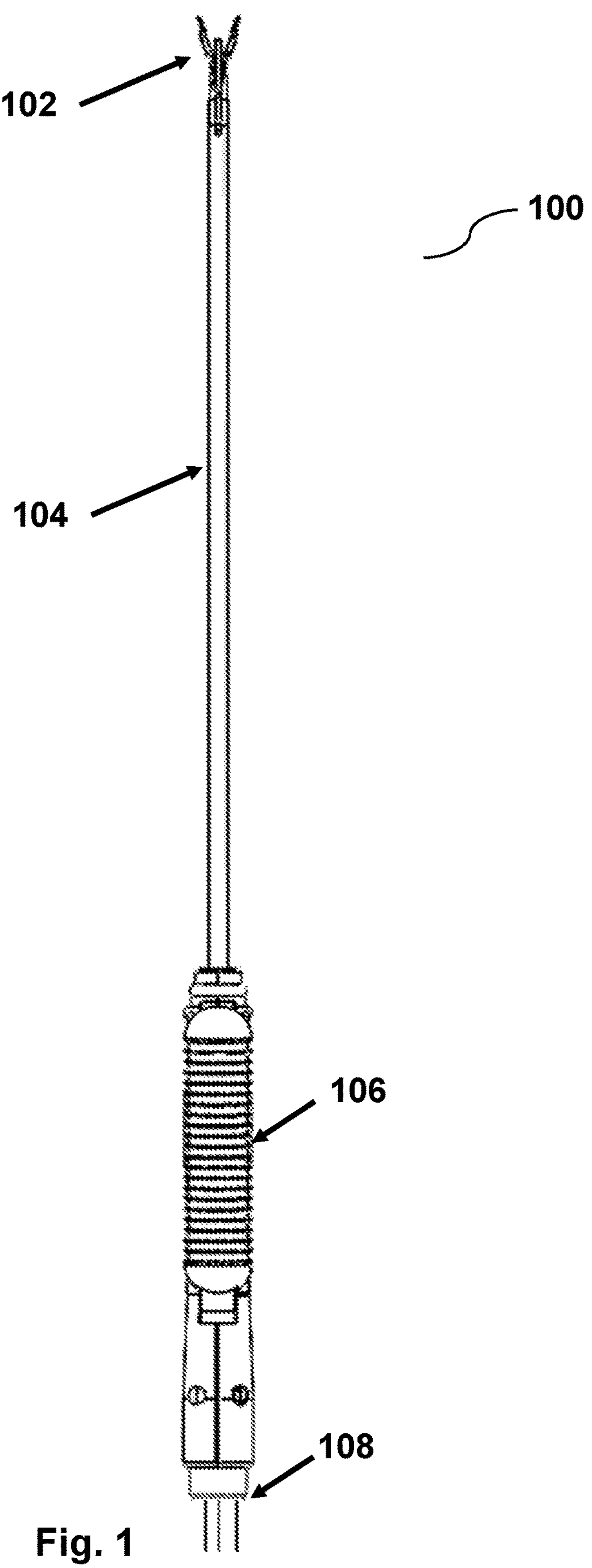
FIG. 1 shows a drawing describing an embodiment of a surgical instrument.
Figure 2:
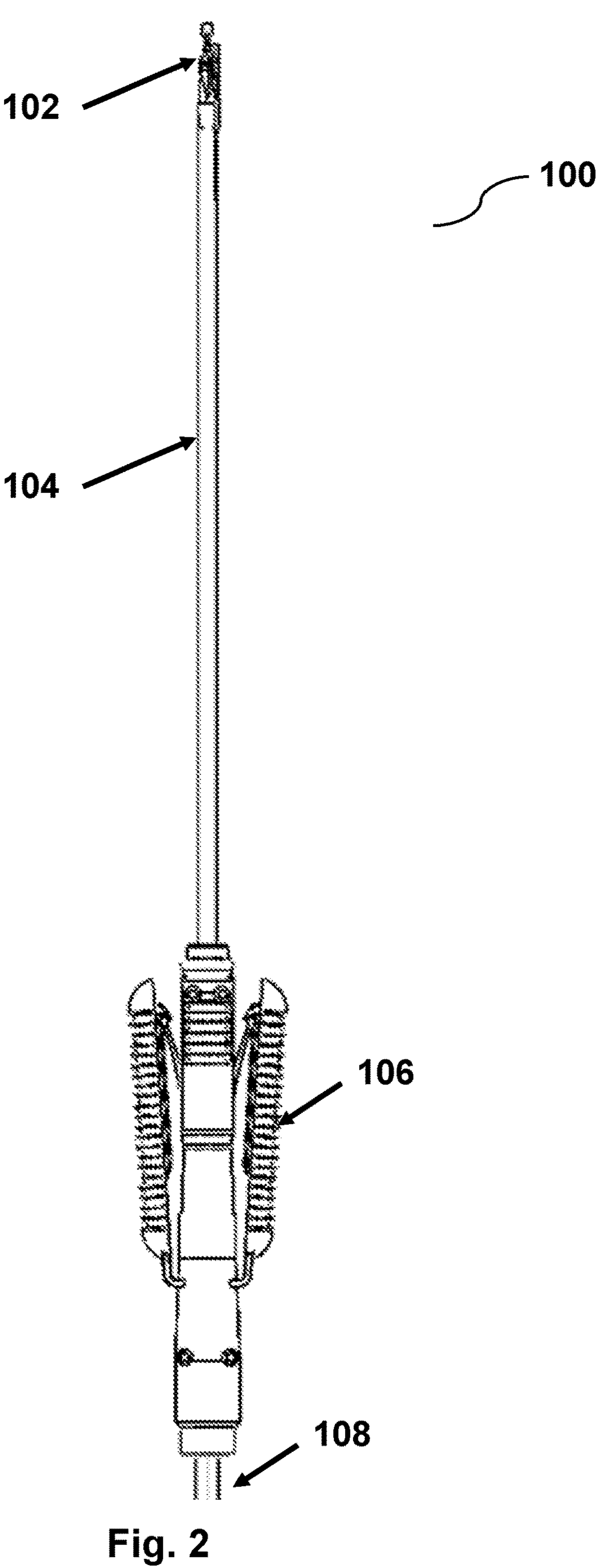
FIG. 2 shows a drawing describing an embodiment of a surgical instrument in a further perspective.

FIG. 1 shows a drawing of the surgical instrument 100 in a preferred embodiment. The surgical instrument 100 can be tweezers, forceps/clamps or a bipolar coagulation instrument, for example. The surgical instrument comprises two jaw portions 102 at the distal end of the instrument, which are connected by a shaft 104 to the gripping portion 106 at the proximal end of the instrument. The gripping portion contains an electrical connector and/or a rinsing connector 108. The connector 108 is formed in the shape of a cable and/or rinsing connector firmly connected to the proximal end of the gripping portion 106. FIG. 2 shows the surgical instrument 100 from a perspective rotated by 90° in relation to FIG. 1.

Figure 3:
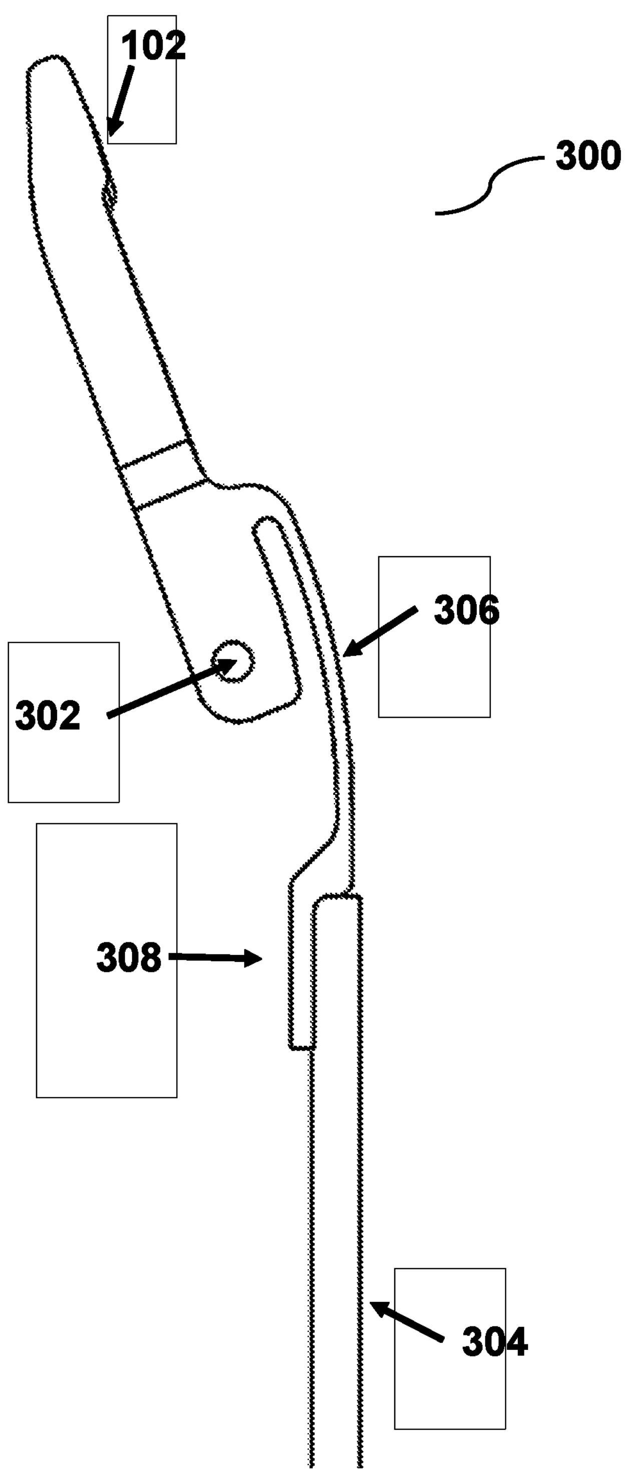
FIG. 3 shows a drawing describing an embodiment of a component of the distal end of the surgical instrument.

FIG. 3 shows a drawing of a component 300 in an embodiment in which the jaw portions 102 are each mounted on the shaft 104 via a rotary bearing or an axis of rotation 302 with a traction cable or a push rod 304. At least one of the jaw portions 102 is connected to the traction cable or the push rod 304 in a direct and cohesive connection 308 via a spring element 306. The two jaw portions can therefore each be actuated by means of a traction cable or a push rod. The jaw portions 102 and spring element 306 are preferably integrally formed. The axis of rotation comprises a hole or bore at the distal end of the shaft.

Figure 4:
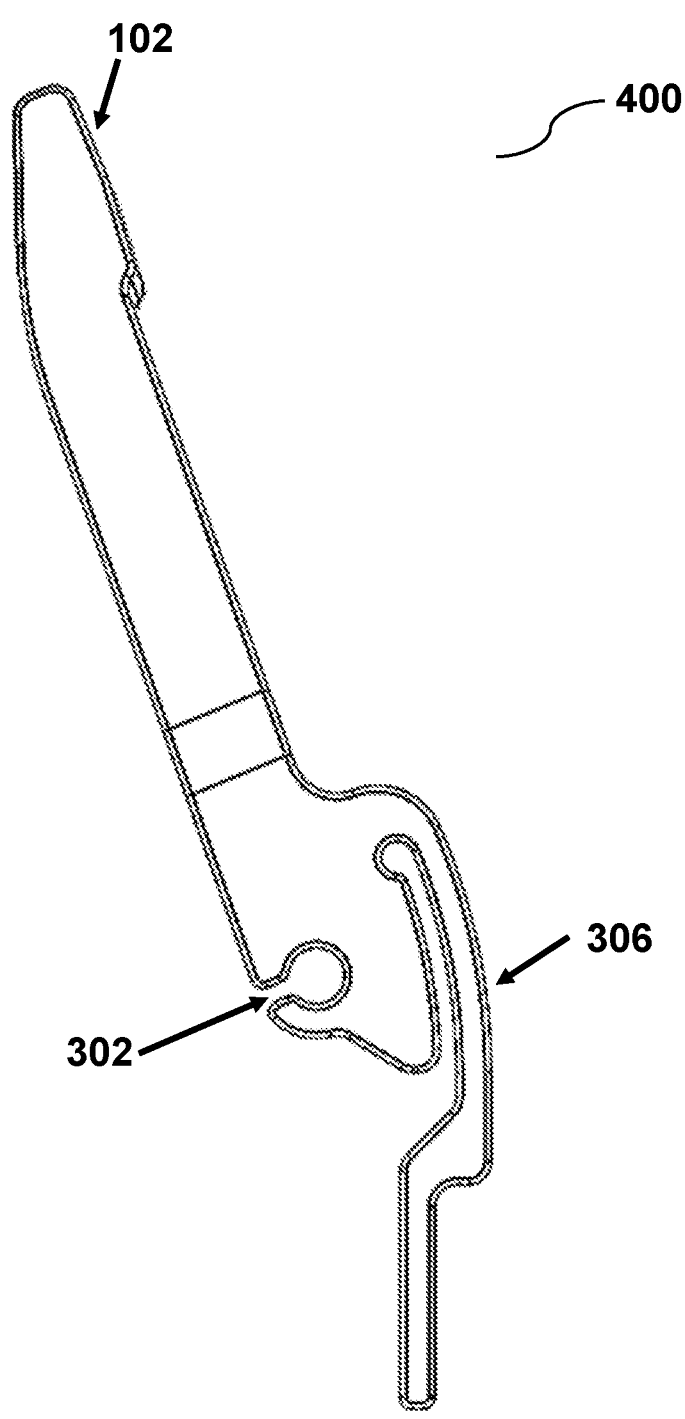
FIG. 4 shows a drawing describing an embodiment of a component of the distal end of the surgical instrument with an alternative embodiment of the axis of rotation.

FIG. 4 shows a component 400 with an alternative configuration of the axis of rotation 302. The axis of rotation 302 comprises a recess here.

The spring element 306 can be formed by a leaf spring or a leaf spring section as an extension of the shaft 104. Alternatively, it can be formed by a leaf spring section as an extension of the traction cable or the push rod 304. The spring element 306 represents an embodiment of the suspension of the instrument 100 described above. In this case, the jaw, which is formed by the jaw portions 102, is held in an open or closed position in a rest position of the instrument 100, depending on the configuration.

Figure 5:
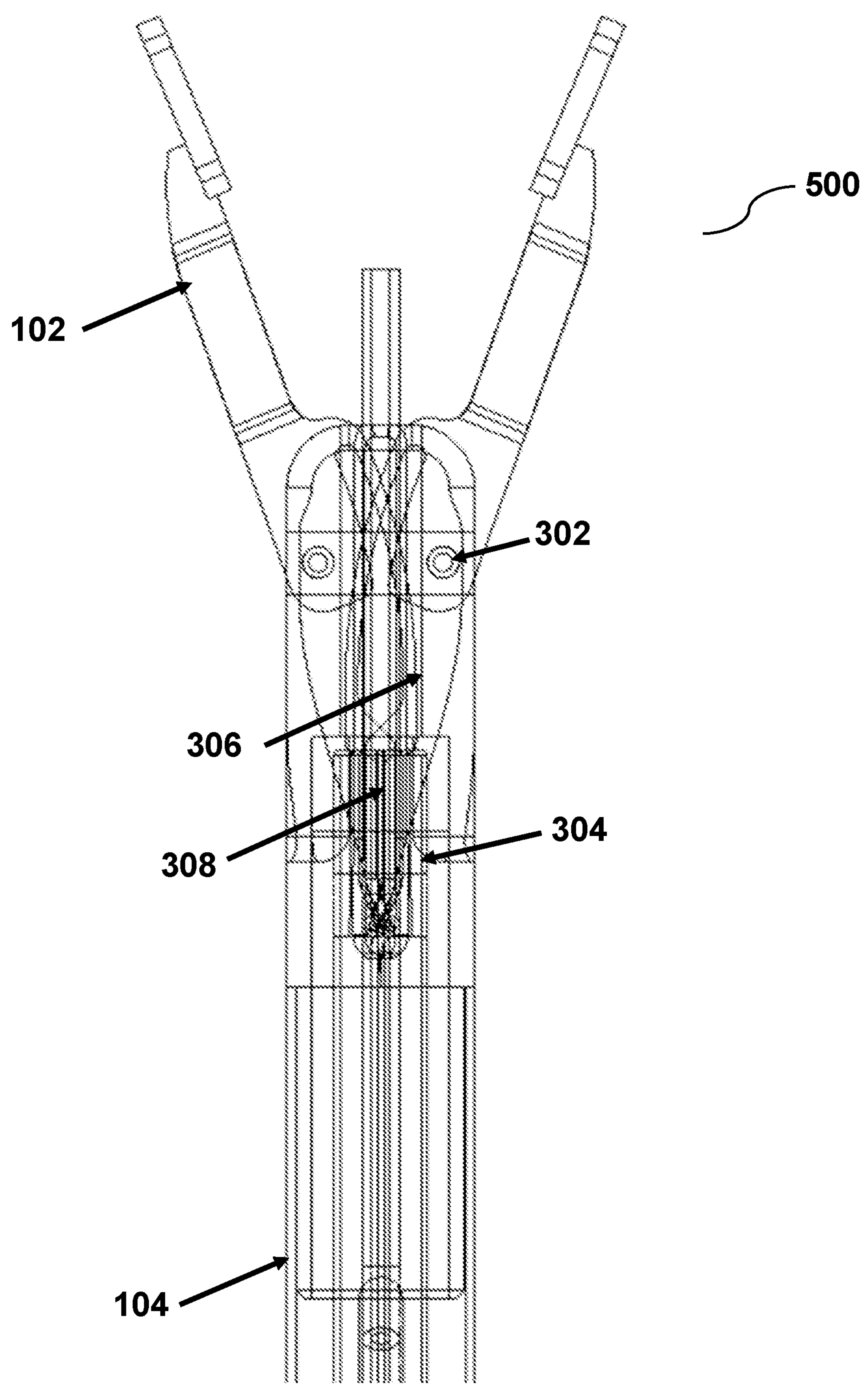
FIG. 5 shows a drawing describing an embodiment of the distal end of the surgical instrument.
Figure 6:
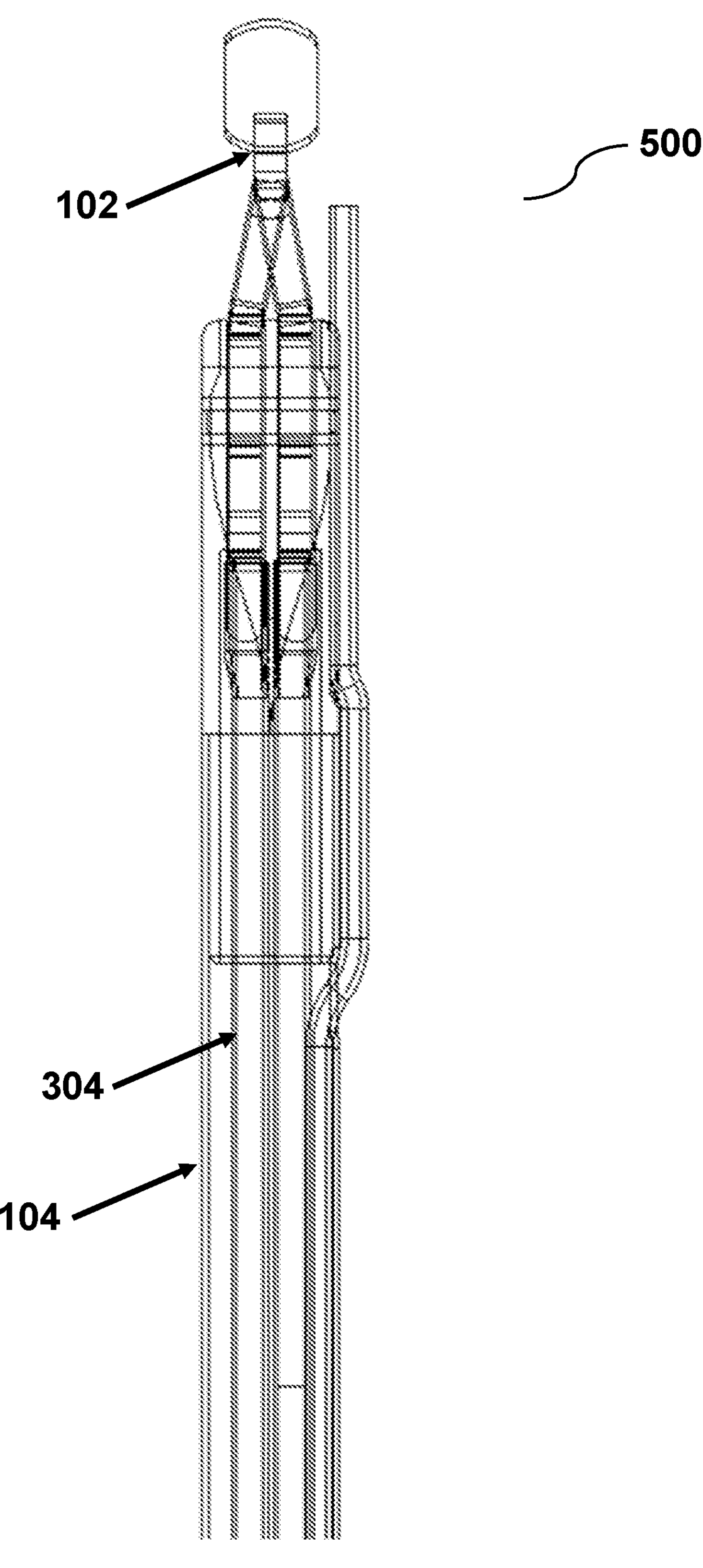
FIG. 6 shows a drawing describing an embodiment of the distal end of the surgical instrument in a further perspective.

FIG. 5 shows the distal end 500 of the instrument consisting of two components 300 in such a resting position. FIG. 6 shows this distal end of the instrument from a perspective rotated by 90° in relation to FIG. 5.

Figure 7:
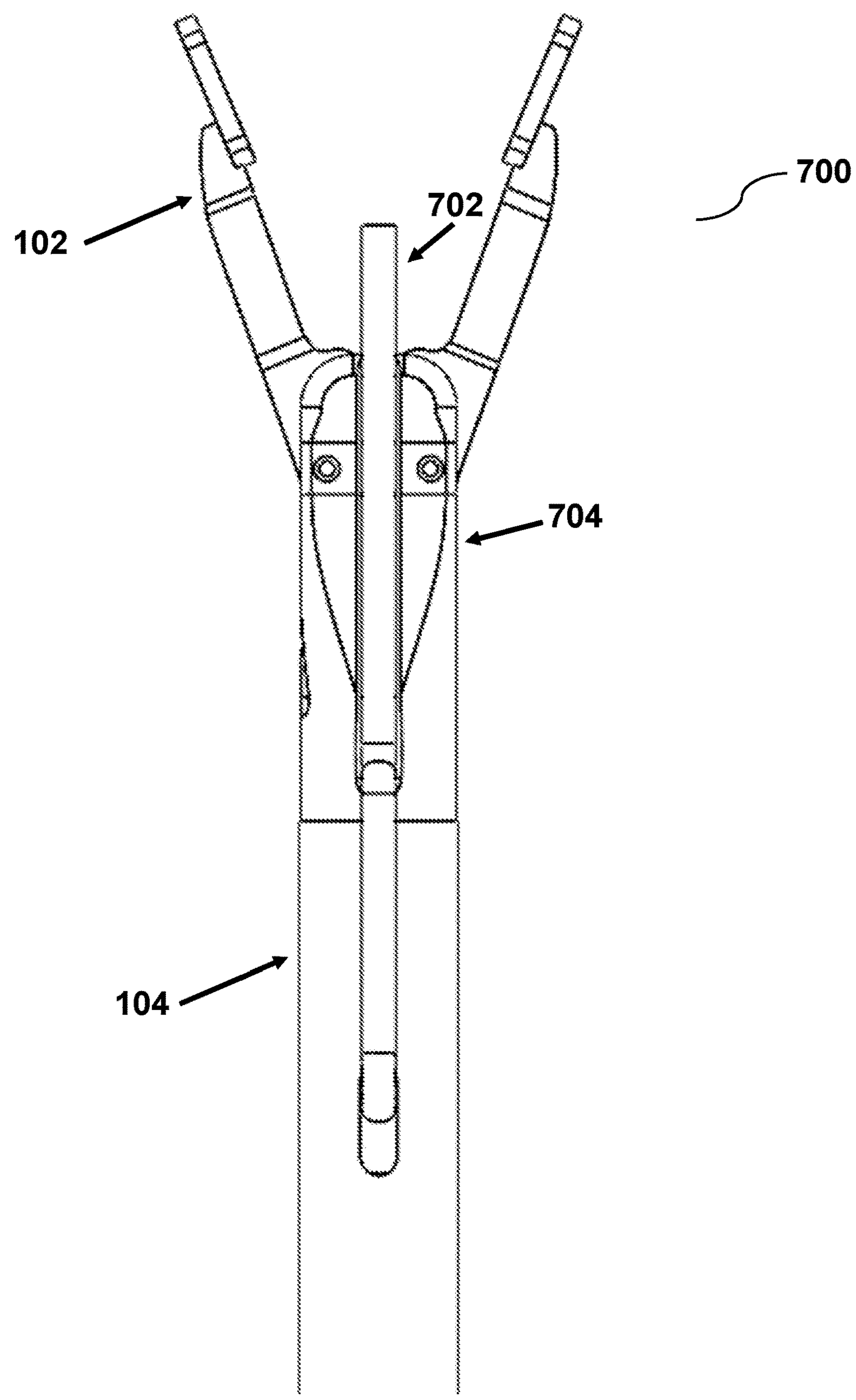
FIG. 7 shows a drawing describing an alternative embodiment of the distal end of the surgical instrument.

FIG. 7 shows the distal end 700 of the instrument with the rinsing tube 702 running from the inside to the outside. Furthermore, here too the jaw portions are mounted so as to be rotatable about the axes of rotation 302 which are located in the head piece 704 of the shaft 104.

Figure 8:
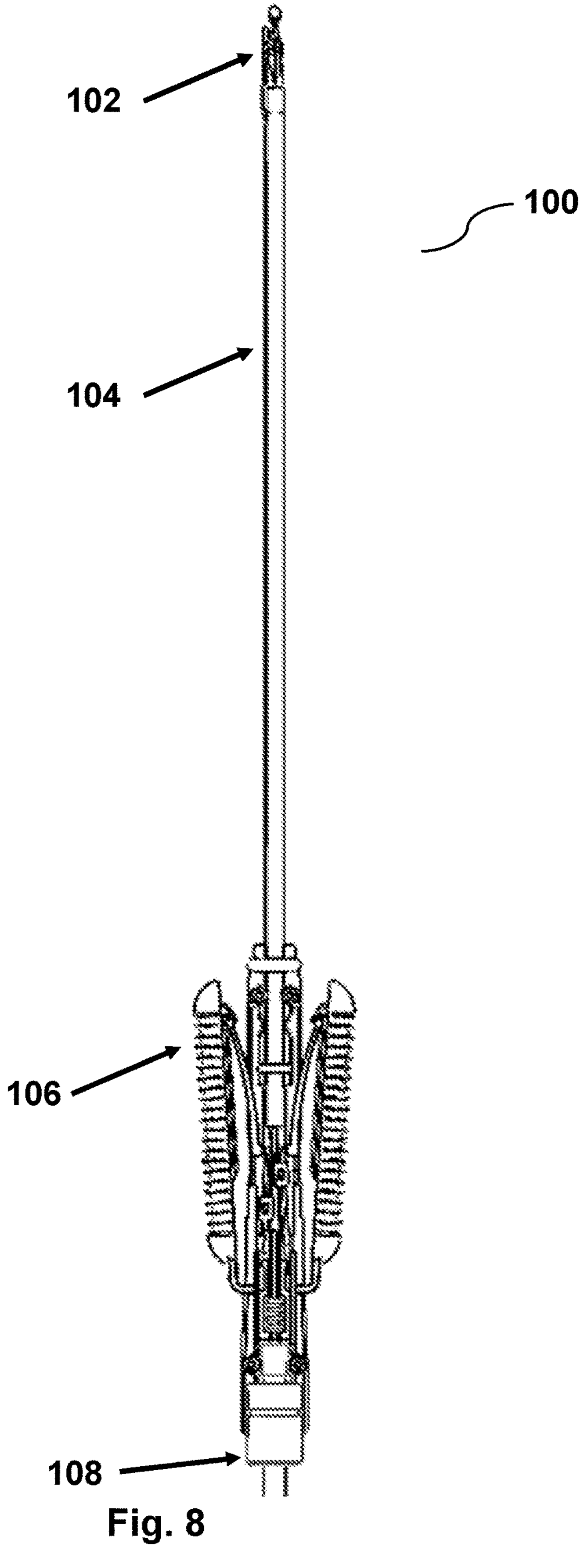
FIG. 8 shows a drawing describing an embodiment of a surgical instrument in a further perspective with details of a gripping portion.
Figure 9:
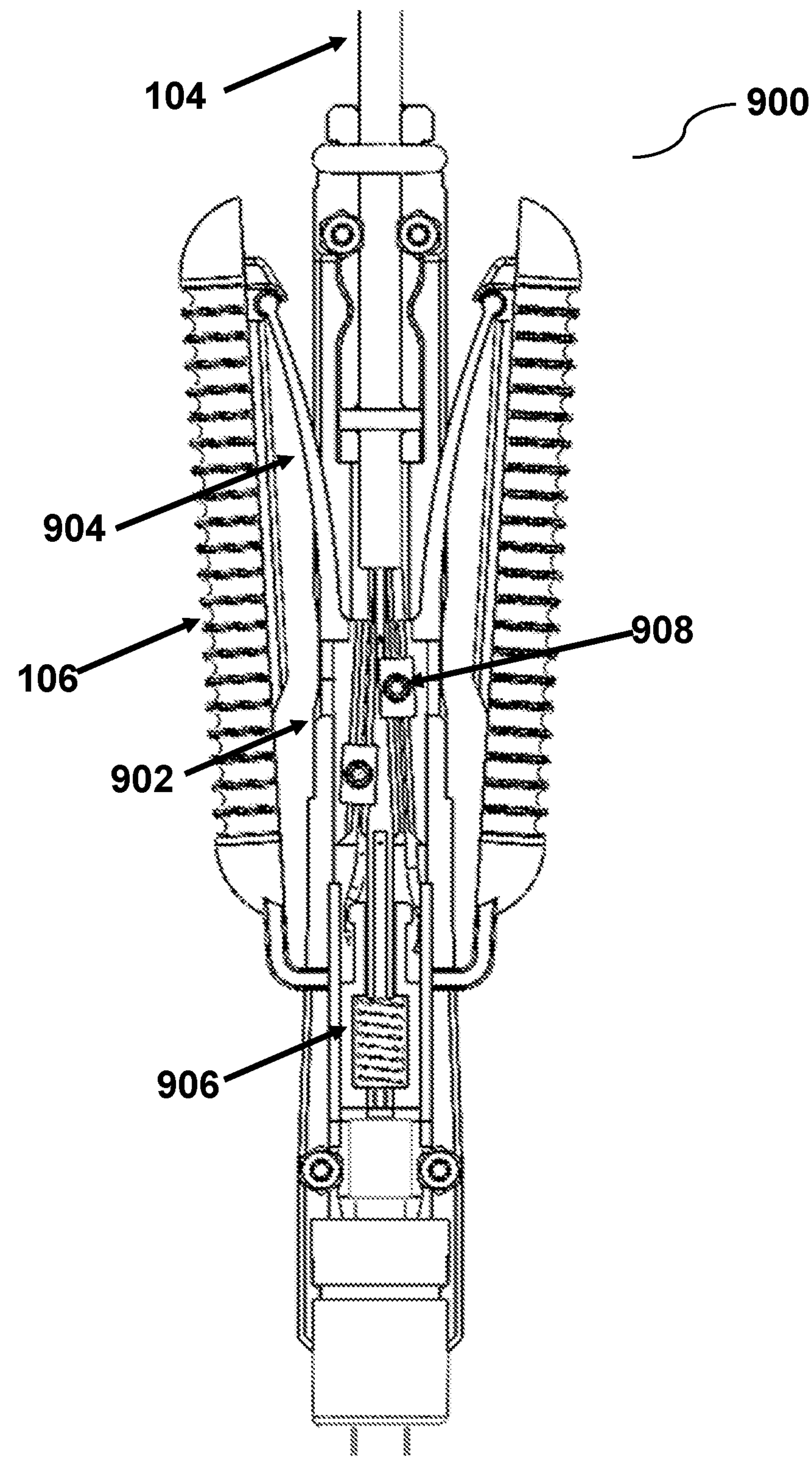
FIG. 9 shows a drawing describing an embodiment of a gripping portion.

FIG. 8 shows a drawing of the surgical instrument 100 illustrating the gripping portion 106. FIG. 9 shows a configuration 900 of the gripping portion 106 of the surgical instrument 100. The traction cables or push rods 304 run in the shaft 104 and are connected to a displacement carriage 902 in the gripping portion 106. In one embodiment, the traction cables or push rods 304 are connected to the displacement carriage 902 by drivers 908, in particular clamping bushes. In one embodiment, the gripping portion 106 includes two spring arms 904 that rest on opposite sides of the interior of the gripping portion 106, respectively. The spring arms 106 are also connected to the displacement carriage 902. The gripping portion 106 contains additional spring portions 906, which are formed in particular by compression springs or restoring springs. The additional spring portions increase the spring force of the spring arms 904.

Figure 10:
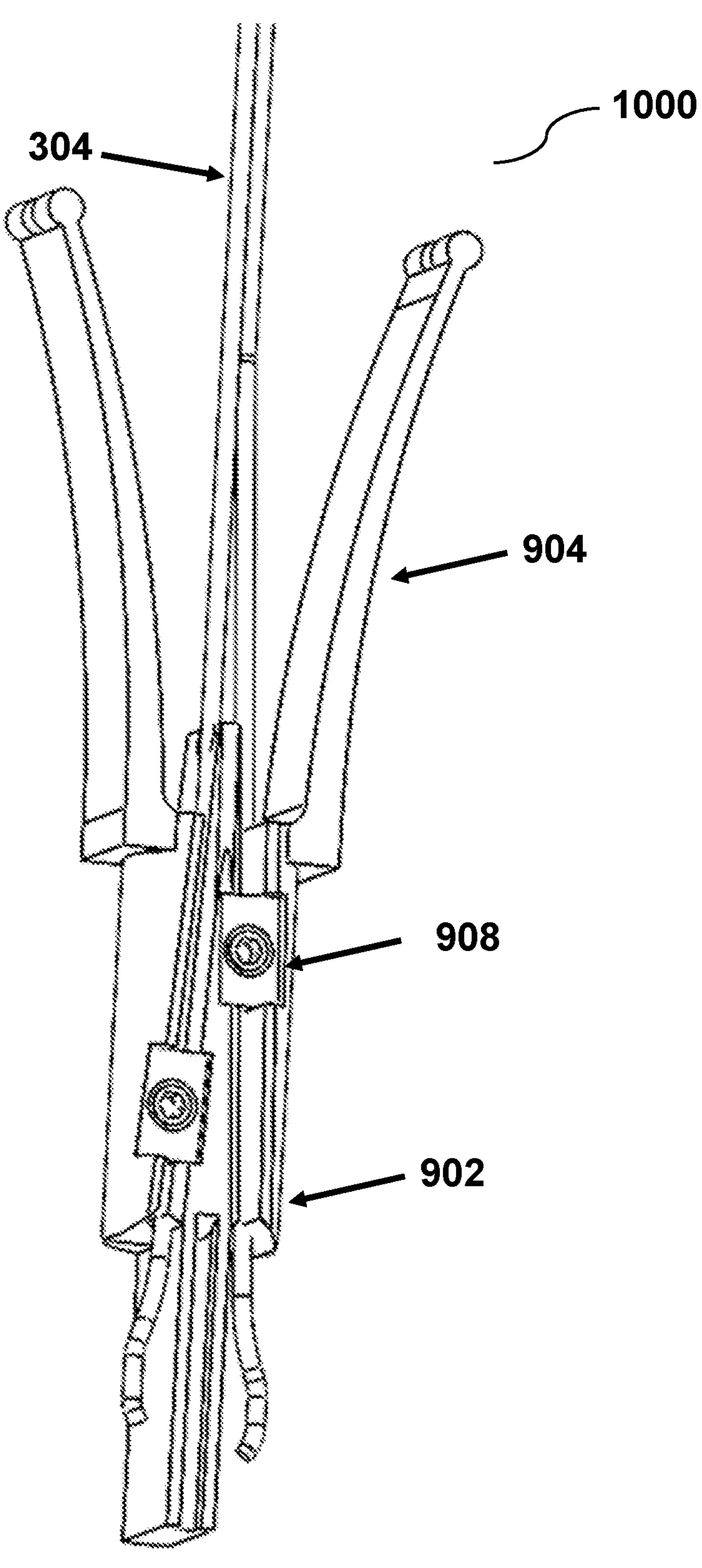
FIG. 10 shows a drawing describing an embodiment of the connection of the traction cable to the displacement carriage by means of clamping bushes.

FIG. 10 shows a portion of the gripping portion 106 of the surgical instrument 100. An embodiment 1000 is shown, wherein the connection of the traction cable or the push rod 304 to the displacement carriage 902 is realised by means of a clamping bush 908.

Figure 11:
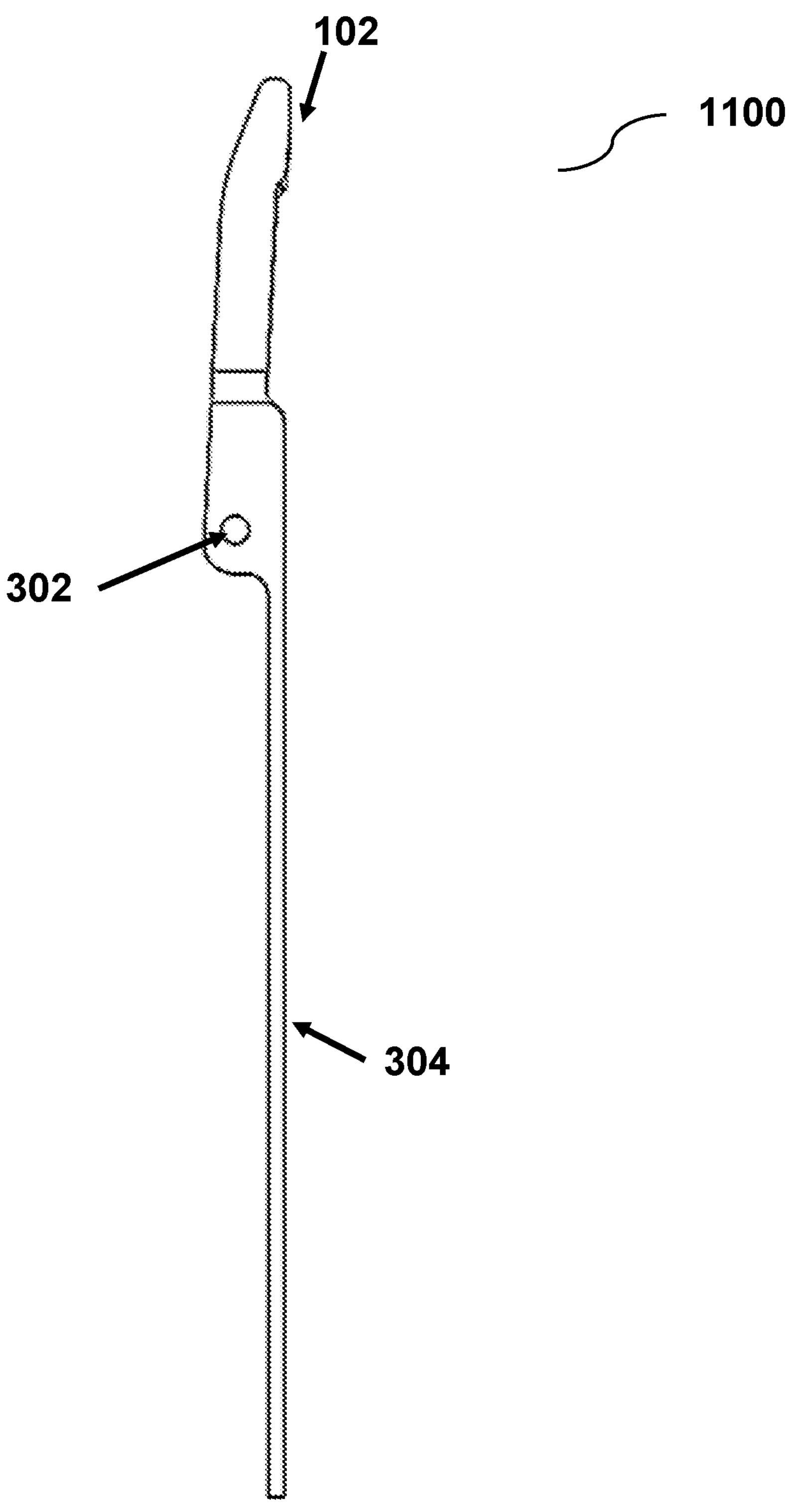
FIG. 11 shows a drawing describing an integrated embodiment with a traction cable/push rod attached directly to the jaw portion.

FIG. 11 describes an alternative embodiment 1100 of the component 300, in which the jaw portion 102 is directly integrally or cohesively connected to a traction cable or a push rod 304 via a rotary bearing or an axis of rotation 302. As a result, the spring element 306 from FIGS. 3-6 can be omitted. The axis of rotation 302 comprises a hole or bore at the distal end of the shaft.

Overall, the invention includes a plurality of options for the suspension of the spring-supported single-joint instrument. The suspension can be formed by a spring element 306 on the jaw portions 102 together with the integrated spring arm 904 in the gripping portion 106. This is possible, for example, by combining the component 300 in FIG. 3 and a gripping portion as in FIG. 9 without a compression spring 906. Alternatively, the suspension can only be formed by a compression spring 906 together with the integrated spring arm 904 in the gripping portion 106. In a further alternative embodiment, the suspension can be formed both by the spring elements 306 on the jaw portions 102 together with the integrated spring arm 904 in the gripping portion 106 and by a compression spring 906 together with the integrated spring arm 904 in the gripping portion, corresponding to a combination of the configurations from FIG. 3 and FIG. 9. Alternatively, the suspension without a spring arm 904 can be realised only via a spring element 306 or only via a compression spring 906 or a combination of a spring element 306 and a compression spring 906.

The described features of each configuration can thus be combined with the features of other configurations.

LIST OF REFERENCE NUMERALS

100 surgical instrument
102 jaw portion
104 shaft
106 gripping portion
108 electric connector and/or rinsing connector
300 component on the distal end of the surgical instrument
302 axis of rotation
304 traction cable or push rod
306 spring element
308 cohesive connection
400 alternative component on the distal end of the surgical instrument
500 distal end of the surgical instrument
700 alternative distal end of the surgical instrument
702 rinsing tube
704 head piece of the shaft 104
900 configuration of the gripping portion 106
902 displacement carriage
904 spring arm
906 pressure spring
908 driver
1000 configuration of the traction cable/push rod connection to the displacement carriage
1100 integral embodiment of jaw portion and traction cable/push rod

The invention claimed is:

1. A surgical instrument (100) comprising two jaw portions (102), at least one of which is rotatably mounted via an axis of rotation (302) at a distal end of a shaft (104) and is connected via a traction cable or a push rod (304) to a gripping portion (106) at a proximal end of the shaft (104), wherein jaws formed by each of the jaw portions (102) is held in an open or closed position by means of a suspension when the instrument (100) is at rest, wherein the suspension comprises spring elements (306) which each connect one of the jaw portions (102) to the traction cable or the push rod (304), and, wherein the spring elements (306) are each connected to the traction cable or the push rod (304) by at least one of: cohesively (308) and integrally.

2. The surgical instrument (100) according to claim 1, wherein the spring elements (306) are each formed integrally with one of the jaw portions (102).

3. The surgical instrument (100) according to claim 1, wherein the spring elements (306) each comprise at least a portion of a leaf spring.

4. The surgical instrument (100) according to claim 1, wherein the suspension further comprises at least one spring arm (904) which is located in the gripping portion (106).

5. The surgical instrument (100) according to claim 1, wherein the instrument (100) further comprises at least one of an electrical connector and a rinsing connector (108) provided at a proximal end of the gripping portion (106).

6. The surgical instrument according to claim 1, wherein the suspension further comprises at least one compression spring (906) which is located in the gripping portion (106).

7. The surgical instrument according to claim 6, wherein the at least one compression spring is located adjacent to a proximal end of the gripping portion (106).

* * * * *